United States Patent
Pallikaris et al.

(10) Patent No.: US 7,156,859 B2
(45) Date of Patent: Jan. 2, 2007

(54) DEVICE FOR SEPARATING THE EPITHELIUM LAYER FROM THE SURFACE OF THE CORNEA OF AN EYE

(75) Inventors: Ioannis Pallikaris, Gazi of Heraklion (GR); Harilaos S. Ginis, Heraklion (GR)

(73) Assignee: FOS Holding S.A., Luxembourg (LU)

( * ) Notice: Subject to any disclaimer, the term of this patent is extended or adjusted under 35 U.S.C. 154(b) by 0 days.

(21) Appl. No.: 09/911,356

(22) Filed: Jul. 23, 2001

(65) Prior Publication Data

US 2003/0018347 A1 Jan. 23, 2003

(51) Int. Cl.
*A61F 9/00* (2006.01)

(52) U.S. Cl. .................................... 606/166; 604/294

(58) Field of Classification Search .............. 606/166, 606/167, 5, 6, 107; 604/294
See application file for complete search history.

(56) References Cited

U.S. PATENT DOCUMENTS

| | | | |
|---|---|---|---|
| 2,881,500 A | 4/1959 | Furness | |
| 4,198,132 A | 4/1980 | Seger et al. | |
| 4,381,007 A | 4/1983 | Doss | |
| 4,417,579 A * | 11/1983 | Soloviev et al. | 606/166 |
| 4,659,584 A * | 4/1987 | Schilk | 604/294 |
| 4,662,370 A | 5/1987 | Hoffmann et al. | |
| 4,665,914 A * | 5/1987 | Tanne | 606/166 |
| 4,688,570 A | 8/1987 | Kramer et al. | |
| 4,770,172 A | 9/1988 | L'Esperance, Jr. | |
| 4,773,414 A | 9/1988 | L'Esperance, Jr. | |
| 4,775,361 A | 10/1988 | Jacques et al. | |
| 4,838,266 A | 6/1989 | Koziol et al. | |
| 4,840,175 A | 6/1989 | Peyman | |
| 4,844,060 A | 7/1989 | Krumeich | |
| 4,865,033 A | 9/1989 | Krumeich et al. | |
| 4,884,570 A | 12/1989 | Krumeich et al. | |

(Continued)

OTHER PUBLICATIONS

Ioannis G. Pallikaris, MD, Maria E. Papatzanaki, MD, Evdoxia Z. Stathi, MD Oliver Frenschook, and Anthimos Georgiadis, PhD, *Laser in Situ Keratomileusis*, Lasers in Surgery and Medicine, vol. 10 pp. 463–468, 1990.

(Continued)

FOREIGN PATENT DOCUMENTS

| | | |
|---|---|---|
| DE | 38 38 253 A1 | 5/1990 |
| DE | 201 15 585 U1 | 2/2002 |
| EP | 0 659 955 B1 | 1/1997 |
| EP | 0 873 735 A1 | 10/1998 |
| EP | 0 956 840 A2 | 11/1999 |
| EP | 1 114 628 A1 | 7/2001 |
| FR | 2 691 625 A3 | 12/1993 |
| WO | WO 94/17851 | 8/1994 |
| WO | WO 98/53774 | 12/1998 |
| WO | WO 01/93791 A1 | 12/2001 |
| WO | WO 01/97729 A1 | 12/2001 |
| WO | WO 02/020683 A2 | 1/2002 |
| WO | WO 03/009789 A1 | 2/2003 |
| WO | WO 03/026542 A1 | 4/2003 |

*Primary Examiner*—Julian W. Woo
*Assistant Examiner*—Victor Nguyen
(74) *Attorney, Agent, or Firm*—Brinks Hofer Gilson & Lione (57) ABSTRACT

An automated mechanical device separates the epithelial layer of a cornea from the cornea. The device includes a separator such as a plate, wire or dull blade. The device can preserve a separated epithelial layer as a disk without rupturing the disk and without substantial epithelial cell loss. The epithelial layer is separated from the cornea without cutting the cornea.

77 Claims, 9 Drawing Sheets

U.S. PATENT DOCUMENTS

| | | | | |
|---|---|---|---|---|
| 4,955,894 | A | 9/1990 | Herman | |
| 5,011,498 | A | 4/1991 | Krumeich et al. | |
| 5,108,388 | A | 4/1992 | Trokel | |
| 5,108,412 | A * | 4/1992 | Krumeich et al. | 606/166 |
| 5,133,726 | A * | 7/1992 | Ruiz et al. | 606/166 |
| 5,196,027 | A | 3/1993 | Thompson et al. | |
| 5,215,104 | A * | 6/1993 | Steinert | 128/898 |
| 5,279,611 | A | 1/1994 | McDonnell et al. | |
| 5,312,330 | A | 5/1994 | Klopotek | |
| 5,312,413 | A * | 5/1994 | Eaton et al. | 606/107 |
| 5,318,047 | A | 6/1994 | Davenport et al. | |
| 5,319,424 | A * | 6/1994 | Tomiyama et al. | 399/174 |
| 5,323,788 | A | 6/1994 | Silvestrini et al. | |
| 5,395,385 | A | 3/1995 | Kilmer et al. | |
| 5,423,801 | A | 6/1995 | Marshall et al. | |
| 5,437,658 | A | 8/1995 | Muller et al. | |
| 5,462,739 | A * | 10/1995 | Dan et al. | 424/427 |
| 5,490,849 | A | 2/1996 | Smith | |
| 5,492,135 | A | 2/1996 | DeVore et al. | |
| 5,496,339 | A | 3/1996 | Koepnick | |
| 5,505,723 | A | 4/1996 | Muller | |
| 5,549,597 | A | 8/1996 | Shimmick et al. | |
| 5,549,632 | A | 8/1996 | Lai | |
| 5,554,155 | A * | 9/1996 | Awh et al. | 606/16 |
| 5,599,341 | A | 2/1997 | Mathis et al. | |
| 5,613,965 | A | 3/1997 | Muller | |
| 5,630,810 | A | 5/1997 | Machat | |
| 5,632,757 | A | 5/1997 | Arnott | |
| 5,647,865 | A | 7/1997 | Swinger | |
| 5,649,943 | A | 7/1997 | Amoils | |
| 5,658,303 | A | 8/1997 | Koepnick | |
| 5,676,679 | A | 10/1997 | Simon et al. | |
| 5,685,998 | A | 11/1997 | Shannon et al. | |
| 5,690,657 | A | 11/1997 | Koepnick | |
| 5,699,810 | A | 12/1997 | Pallikaris | |
| 5,700,274 | A | 12/1997 | Feaster | |
| 5,711,762 | A | 1/1998 | Trokel | |
| 5,722,427 | A | 3/1998 | Wakil et al. | |
| 5,722,971 | A | 3/1998 | Peyman | |
| 5,735,843 | A | 4/1998 | Trokel | |
| 5,740,803 | A | 4/1998 | Gray et al. | |
| 5,741,245 | A | 4/1998 | Cozean et al. | |
| 5,779,696 | A | 7/1998 | Berry et al. | |
| 5,795,351 | A | 8/1998 | Clapham | |
| 5,807,380 | A | 9/1998 | Dishler | |
| 5,807,381 | A | 9/1998 | Lieberman | |
| 5,833,701 | A | 11/1998 | Gordon | |
| 5,851,213 | A * | 12/1998 | Berleth et al. | 606/167 |
| 5,857,995 | A | 1/1999 | Thomas et al. | |
| 5,941,874 | A | 8/1999 | Hohla | |
| 5,964,748 | A | 10/1999 | Peyman | |
| 5,970,984 | A | 10/1999 | Wakil et al. | |
| 5,975,351 | A | 11/1999 | DeLacerda | |
| 5,980,543 | A | 11/1999 | Carriazo et al. | |
| 5,984,916 | A | 11/1999 | Lai | |
| 5,989,272 | A | 11/1999 | Barron et al. | |
| 5,997,559 | A * | 12/1999 | Ziemer | 606/166 |
| 6,006,756 | A | 12/1999 | Shadduck | |
| 6,030,398 | A | 2/2000 | Klopotek | |
| 6,071,293 | A | 6/2000 | Krumeich | |
| 6,083,236 | A | 7/2000 | Feingold | |
| 6,099,541 | A | 8/2000 | Klopotek | |
| 6,110,202 | A | 8/2000 | Barraquer et al. | |
| 6,126,668 | A * | 10/2000 | Bair et al. | 606/166 |
| 6,129,723 | A | 10/2000 | Anderson et al. | |
| 6,132,421 | A | 10/2000 | Clapham | |
| 6,162,210 | A | 12/2000 | Shadduck | |
| 6,171,336 | B1 | 1/2001 | Sawusch | |
| 6,203,538 | B1 | 3/2001 | Peyman | |
| 6,217,571 | B1 | 4/2001 | Peyman | |
| 6,221,067 | B1 | 4/2001 | Peyman | |
| 6,241,721 | B1 | 6/2001 | Cozean et al. | |
| 6,254,619 | B1 | 7/2001 | Garabet et al. | |
| 6,264,648 | B1 | 7/2001 | Peyman | |
| 6,280,470 | B1 | 8/2001 | Peyman | |
| 6,293,938 | B1 | 9/2001 | Muller et al. | |
| 6,302,896 | B1 | 10/2001 | Carriazo et al. | |
| 6,306,075 | B1 | 10/2001 | Shadduck | |
| 6,322,216 | B1 | 11/2001 | Yee et al. | |
| 6,331,177 | B1 | 12/2001 | Munnerlyn et al. | |
| 6,379,370 | B1 | 4/2002 | Feinsod | |
| 6,409,345 | B1 | 6/2002 | Molebny et al. | |
| 6,436,093 | B1 | 8/2002 | Ruiz et al. | |
| 6,464,692 | B1 | 10/2002 | Ruiz et al. | |
| 6,497,701 | B1 | 12/2002 | Shimmick et al. | |
| 6,506,198 | B1 * | 1/2003 | Amano | 606/166 |
| 6,530,916 | B1 | 3/2003 | Shimmick | |
| 6,543,453 | B1 | 4/2003 | Klima et al. | |
| 6,544,286 | B1 | 4/2003 | Perez | |
| 6,559,305 | B1 | 5/2003 | Bergren | |
| 6,589,558 | B1 | 7/2003 | Pallikaris | |
| 6,607,527 | B1 | 8/2003 | Ruiz et al. | |
| 6,623,497 | B1 | 9/2003 | Feingold | |
| 6,626,924 | B1 | 9/2003 | Klopotek | |
| 6,638,271 | B1 | 10/2003 | Munnerlyn et al. | |
| 6,666,855 | B1 | 12/2003 | Yee et al. | |
| 6,673,062 | B1 | 1/2004 | Yee et al. | |
| 6,702,807 | B1 | 3/2004 | Peyman | |
| 6,702,832 | B1 * | 3/2004 | Ross et al. | 606/166 |
| 6,706,036 | B1 | 3/2004 | Lai | |
| 6,730,073 | B1 | 5/2004 | Bruce | |
| 2001/0053917 | A1 | 12/2001 | Lin et al. | |
| 2002/0026101 | A1 | 2/2002 | Bookwalter | |
| 2002/0026240 | A1 | 2/2002 | Pallikaris et al. | |
| 2002/0052596 | A1 | 5/2002 | Pallikaris et al. | |
| 2002/0077640 | A1 | 6/2002 | Metzger | |
| 2003/0011745 | A1 | 1/2003 | Molebny et al. | |
| 2003/0018348 | A1 | 1/2003 | Pallikaris et al. | |
| 2003/0083743 | A1 | 5/2003 | Perez | |
| 2003/0105521 | A1 | 6/2003 | Perez | |
| 2003/0139755 | A1 | 7/2003 | Dybbs | |
| 2003/0220653 | A1 | 11/2003 | Perez | |
| 2004/0059361 | A1 | 3/2004 | Feingold | |
| 2004/0073246 | A1 | 4/2004 | Aufure et al. | |
| 2004/0097955 | A1 | 5/2004 | Feingold | |

OTHER PUBLICATIONS

Stephen L. Trokel, M.D., R. Srinivasan, PhD., and Bodil Baren, B.A., *Excimer Laser Surgery of the Cornea*, vol. 96, No. 6, pp. 710–715, 1983.

David S. Gartry, FRCS, FCOphth, Malcolm G. Kerr Muir, FRCS, FCOphth, John Marshall, Ph.D., *Photorefractive Keratectomy with an Argon Fluoride Excimer Laser: A Clinical Study*, vol. 7, pp. 420–435, Nov./Dec. 1991.

Terry J. Van Der Werff, D.Phil., *A New Single–Parameter Ocular Rigidity Function*, vol. 92, pp. 391–395 (1981).

Winston Roberts, M.D., and J. William Rogers, M.D., *Postural Effects on Pressure and Ocular Rigidity Measurements,* pp. 111–118 (Assumed published prior to filing date).

Peter P. Purslow, PhD, Wojciech S.S. Karwatowski, FROCOphth, *Ocular Elasticity,* pp. 1686–1692 (1996).

Joseph N. Simone, MD and Marc M. Whitacre, MD, *The Effect of Intraocular Gas and Fluid Volume on Intraocular Pressure,* Ophthalmology, vol. 97, No. 2, pp. 238–243 (1990).

John E. Eisenlohr, M.E. Langham and A.E. Maumenee, *Manometric Studies of the Pressure–Volume Relationship in Living and Enucleated Eyes of Individual Human Subjects,* Brit. J. Ophthal., vol. 46, pp. 536–548 (1962).

Richard F. Brubaker, *Tonometry, Clinical Opthalmology,* vol. 3, Chap. 47, pp. 1–7 (Assumed to be published before filing date).

Jonas S. Friedenwald, M.D., *Tonometer Caliberation,* pp. 108–123 (1957).

Carsten Edmund, *Corneal Elasticity and Ocular Rigidity in Normal and Keratoconic Eyes,* Acta Ophthalmologica, vol. 66, pp. 134–140 (1988).

Ephraim Friedman, MD, Sara Krupsky, MD, Anne Marie Lane, MPH, Setsuko S. Oak, Eric S. Friedman, MD, Kathleen Egan, MPH, Evangelos S. Gragoudas, MD, *Ocular Blood Flow Velocity in Age–Related Macular Degeneration,* Ophthalmology, vol. 102, No. 4, pp. 640–646 (1995).

Mark W, Johnson, MD, Dennis P. Han, MD, Kenneth E. Hoffman, MS, *The Effect of Scleral Buckling on Ocular Rigidity,* Ophthalmology, vol. 97, pp. 190–195 (1990).

Evangelos S. Gragoudas, MD, Suresh R. Chandra, MD, Ephraim Friedman, MD, Michael L. Klein, MD, Micael Van Buskirk, MD, *Disciform Degeneration of the Macula,* Arch Ophthalmol, vol. 94, pp. 755–757 (1976).

Ephraim Freidman, MD, *A Hemodynamic Model of the Pathogenesis of Age Related Macular Degeneration,* pp. 1–14 (1997).

Jeffrey B. Robin, MD *Overview of Microkeratomes,* (Assumed to be published before filing date).

Lohmann, Chris P., MD, PhD, "Epi–Lasik Epi–Tome", presented Apr. 2004, Seville, Spain, 47 pages.

Photo using a light microscope of a blade manufactured by GeBauer, evaluated in Athens, Greece, on or about Jun. 2004, One page.

Soloway, Barrie D., "US Clinical Studies with the Epik for E–Lasik" performed by Moria (Epi–Lasik and Lamellar Surgery), presented Sep. 18, 2004, Paris, France, Twenty–three pages.

Gebauer announcements of clinical results for the first 100 Epi–LASIK patients treated in Europe, Mar. 5, 2004, One page.

\* cited by examiner

DEVICE FOR SEPARATING THE EPITHELIUM LAYER FROM THE SURFACE OF THE CORNEA OF AN EYE

BACKGROUND

LASIK (Laser-Assisted In Situ Keratomileusis) is a surgical procedure intended to reduce a person's dependency on glasses or contact lenses. LASIK permanently changes the shape of the cornea, the clear covering of the front of the eye, using an excimer laser. A device, called a microkeratome, is used to cut a flap in the cornea. A hinge is left at one end of this flap. The flap is folded back revealing the stroma, the middlesection of the cornea. Pulses from a computer-controlled laser vaporize a portion of the stroma and the flap is replaced. It is important that the knife used during the LASIK procedure is sharp, otherwise the quality of the procedure and the healing time are poor. Additionally the knife has to be sharp in order to produce consistent and reproducible flaps. There are some complications related to the use of microkeratomes. The most common complication is the creation of an irregular flap, for example, a half flap, buttonhole, or total cup. These complications represent irregular incisions of the cornea, a situation that can permanently degrade visual performance.

Before LASIK, PRK (Photo-Refractive Keratectomy) was used to correct the curvature of the cornea. A physician could scrape away a superficial layer, e.g., the epithelium, of the cornea. After the superficial layer was removed, laser treatment was applied on to the exposed surface of the cornea. A problem existed, however, in that the healing period for the eye typically lasted for a week, much longer than the healing period of LASIK. Also, the patient experienced a lot of pain during healing. Typically in PRK a disposable contact lens is used to cover the treated area of the cornea and help reduce postoperative pain.

In another technique, LASEK (Laser Epithelial Keratomileusis) the epithelial layer is separated from the surface of the cornea in a manner that the separated epithelial layer can be preserved. First, the epithelium is treated with and alcohol solution to partially devitalize it. Once the exact surface area of treatment is determined, a few drops of a weak alcohol solution is applied to the surface of the cornea and allowed to stay in contact with the epithelium for a few seconds. This weak alcohol solution is then rinsed off the surface of the eye. The function of the weak alcohol solution is to loosen the epithelial layer (50 microns) and to allow it to be peeled back in a sheet of epithelial cells, thereby exposing the underlying cornea. This is not to be confused with LASIK, which actually uses a microkeratome instrument to create a flap of both epithelium and the front part of the stromal tissue measuring anywhere between 130 to 180 microns.

In LASEK, the epithelium-only layer is laid back in a similar fashion to LASIK, but consists of only epithelium, not corneal stroma. Once the epithelial cells have been laid out of the way, the laser is applied to the surface of the cornea in the exact same fashion as in PRK. Once the laser treatment has been completed, the epithelial layer is laid back into place and a soft contact lens is placed over the eye as in PRK. The epithelial cells, which were partly devitalized by the weak alcohol solution, are laid over the treatment area and may serve as a facilitator of new epithelium healing underneath. The alcohol-devitalized epithelium falls off the eye, similar to a scab, in 5–10 days. These devitalized epithelial cells do not become the new surface of the eye, but simply serve as a protective agent in addition to the contact lens to facilitate comfort and healing of the new underlying epithelium. Alcohol treatment of the epithelium results in a severe amount of epithelial cell loss, a fact that may render the epithelial disk not usable, due to the reduced durability and adhesion on to the cornea.

Thus, there is a need for an automated corneal epithelium separator that addresses the above problems by separating the epithelial layer as a whole in a mechanical way, not chemical.

BRIEF SUMMARY

To help correct an imperfect vision of a patient's eye, an automated mechanical device separates the epithelial layer from the cornea of a patient's eye from the cornea. After the epithelial layer is separated from the cornea, a laser is used to help correct imperfections in the cornea. Thereafter, the epithelial layer is placed back on the cornea to reduce the visual rehabilitation period and reduce postoperative pain.

In one aspect, the device includes a separator such as a plate, wire or dull blade. The device can preserve a separated epithelial layer as a disk without rupturing the disk and without substantial epithelial cell loss. The epithelial layer is separated from the cornea without cutting the cornea.

DETAILED DESCRIPTION

To help correct an imperfect vision of a patient's eye, an automated mechanical device separates the epithelial layer from the cornea of a patient's eye from the cornea. A separator, such as a plate, wire or dull blade is used to separate the epithelial layer of the cornea from the basal membrane. In this way, the automated mechanical device can preserve the separated epithelial layer as a disk without rupturing the disk and without substantial epithelial cell loss, less than 5–10% loss, to ensure viability and stability of the epithelial disk after replacement on the surface of the cornea. After the epithelial layer is separated from the cornea, a laser is used to help correct imperfections in the cornea. Thereafter, the epithelial layer is placed back on the cornea to aid in the healing process of the eye.

Figure 1:
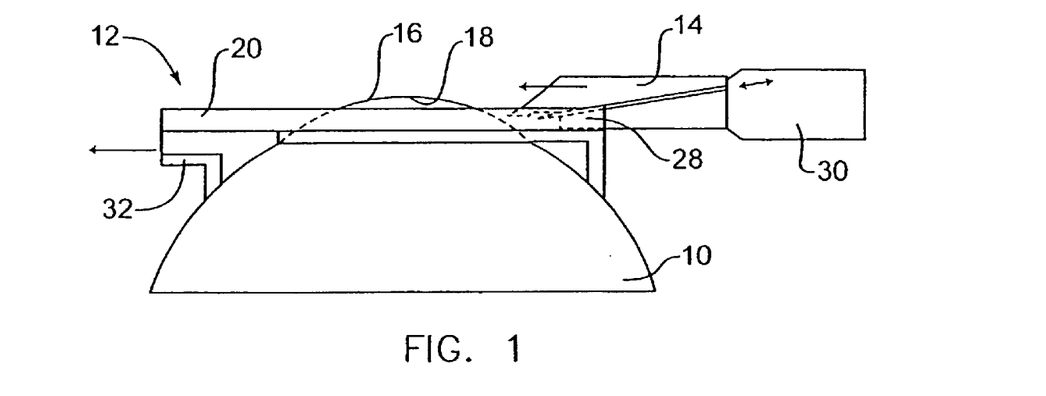
FIG. 1 is a diagram showing a side view of an eye and a cornea separator with a separator located in a first position according to the preferred embodiments.

FIG. 1 is a diagram showing a side view of an eye 10 of a patient and a cornea separator device 12. The cornea separator device 12 includes a separator 14, shown here in a first position located away from the eye 10. The separator 14 includes a device that can scrape the epithelium from the cornea such as a plate, a wire or a knife with a dull edge. The separator 14 removes an epithelium layer 16 located above a corneal surface 18 of the eye 10. The separator 14 is not sharp enough to excise corneal tissue during operation of the cornea separator device 12.

Figure 2:
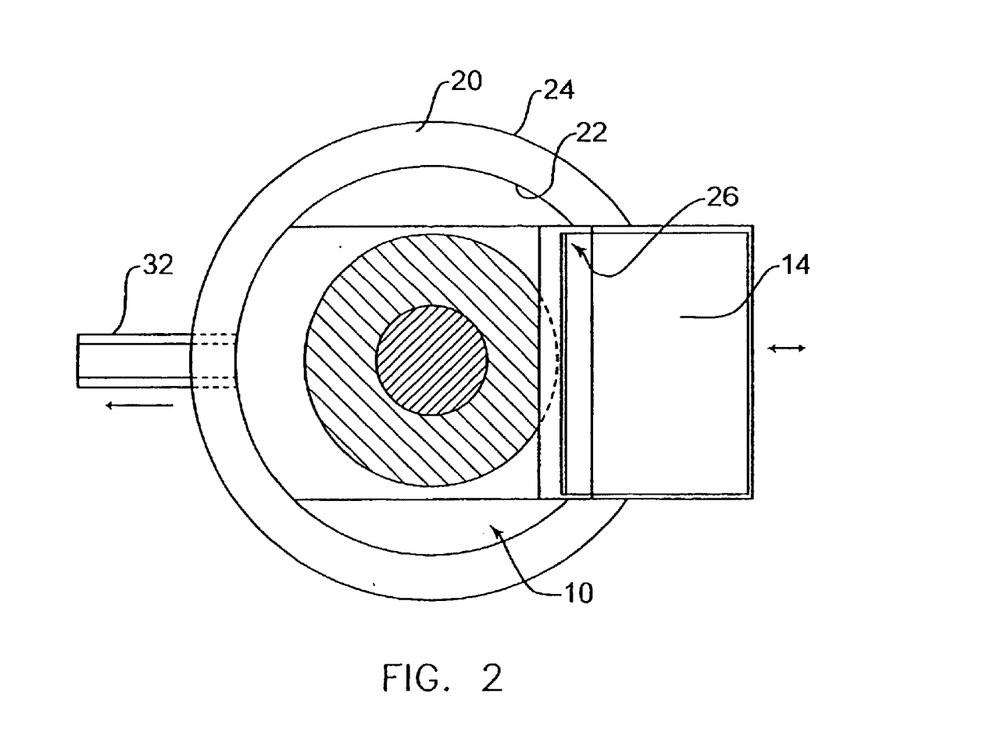
FIG. 2 is a diagram showing a top view of the eye and the separator located in a first position according to the preferred embodiments.

Referring also to FIG. 2, the cornea separator device 12 includes a ring 20 that sits on the eye 10 with its plane parallel to a limbus of the eye. The ring 20 includes an internal diameter 22 ranging from about 10 to about 12 mm and external diameter 24 from about 13 to about 16 mm and including a groove 26 (best seen in FIG. 15). The groove 26 is dimensioned wider than the internal diameter 22. A separator support 28 fits in the groove 26 to carry the separator 14 on a determined travel.

An oscillation device 30 provides motion and vibration to the separator 14. The oscillation device 30 can oscillate the separator 14 either transversely or longitudinally with frequency ranging from about 10 Hz to about 10 KHz. Electromagnetic or piezoelectric forces on the separator 14 can provide the oscillation, or external rotating or vibrating wires can provide the oscillation. To maintain the ring 20 on the eye 10, for example during oscillation, the ring 20 can include a circumferential groove 32 positioned on a side of the eye 10. Suction can be applied to the circumferential groove 32 to ensure stable mounting of the ring 20 to the eye 10.

Figure 3:
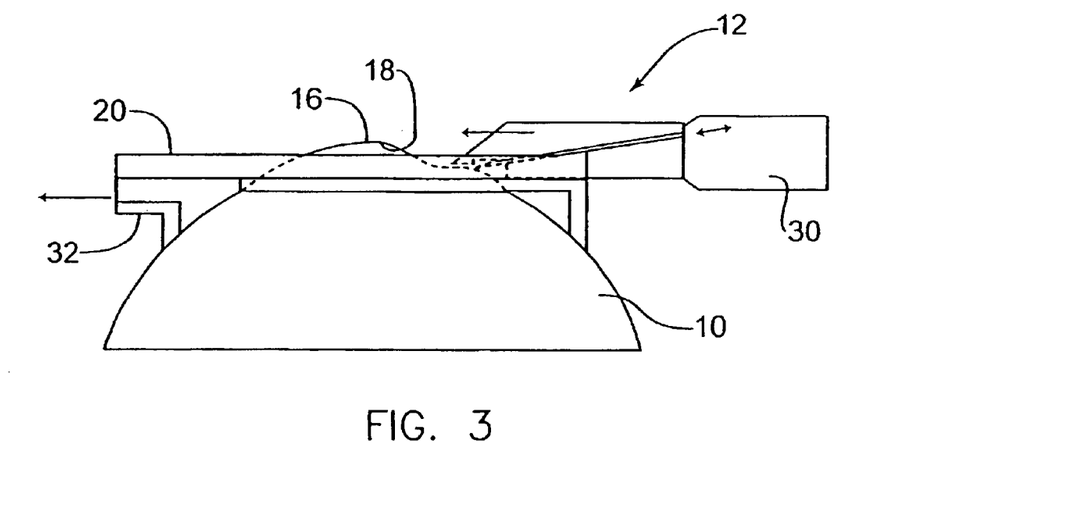
FIG. 3 is a diagram showing a side view of the eye and the separator located in a second position according to the preferred embodiments.
Figure 4:
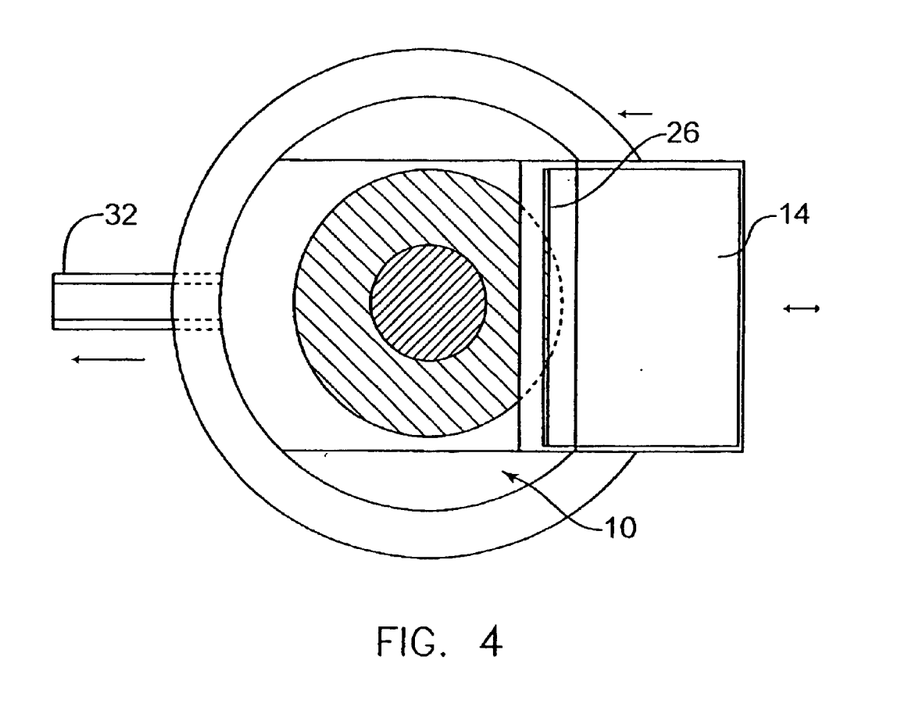
FIG. 4 is a diagram showing a top view of the eye and the separator located in a second position according to the preferred embodiments.

FIGS. 3 and 4 are diagrams showing a side and a top view, respectively, of the eye 10 and the separator 14 located in a second position with respect to the eye. As the separator 14 travels to contact the eye 10, the corneal surface 18 is flattened. To accommodate the travel of the separator 14, the separator support 28 freely slides in the groove 26, for example, when driven by the oscillation device 30.

Figure 5:
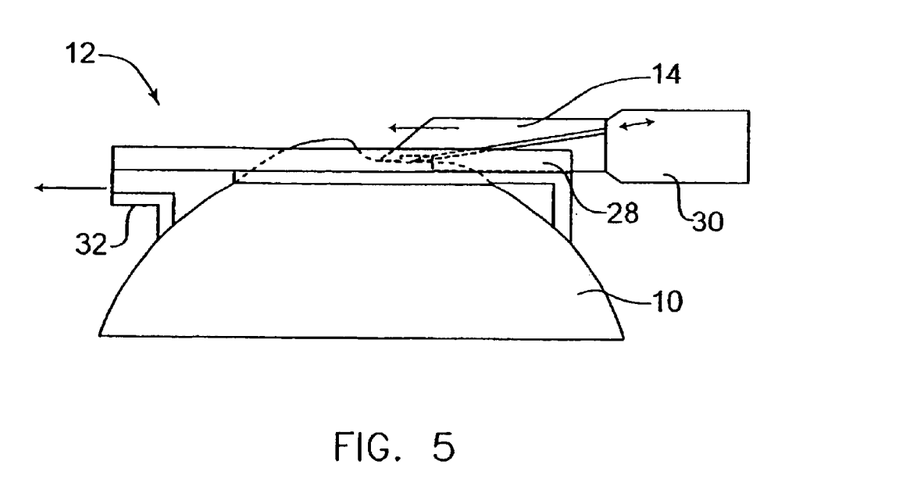
FIG. 5 is a diagram showing a side view of the eye and the separator located in a third position according to the preferred embodiments.
Figure 6:
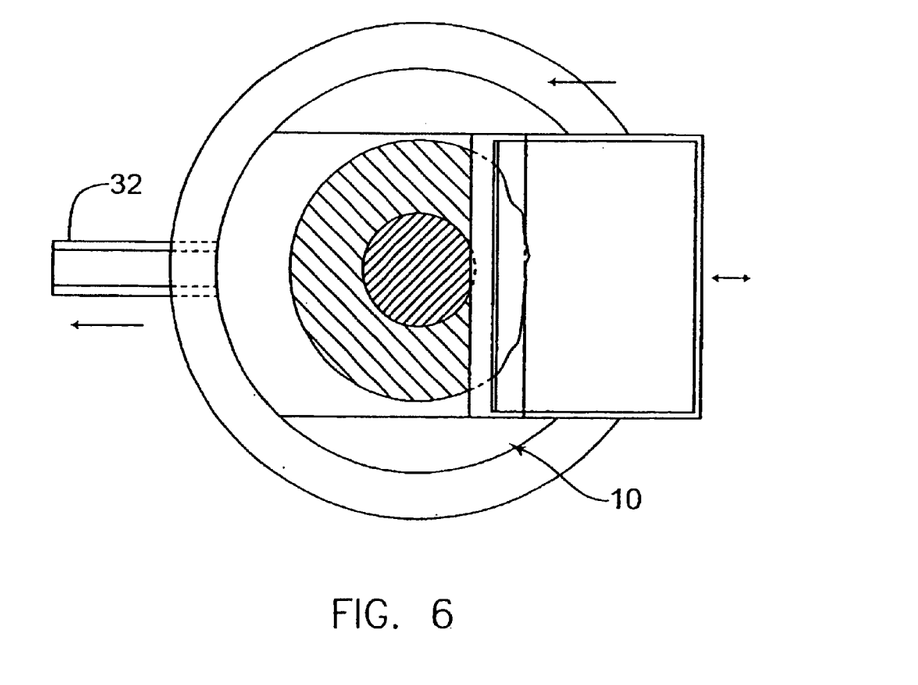
FIG. 6 is a diagram showing a top view of the eye and the separator located in a third position according to the preferred embodiments.

FIGS. 5 and 6 are diagrams showing a side and a top view of the eye 10 and the separator 14 located in a third position. As the separator 14 travels along the cornea 10, the epithelium layer 16 is separated from the cornea. The separator 14 separates the epithelium layer 16 without cutting the cornea 18.

Figure 7:
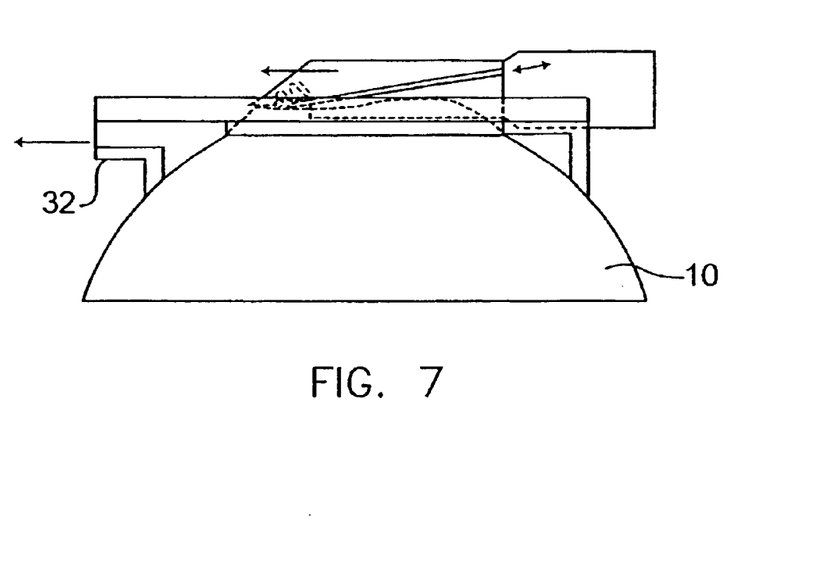
FIG. 7 is a diagram showing a side view of the eye and the separator located in a fourth position according to the preferred embodiments.
Figure 8:
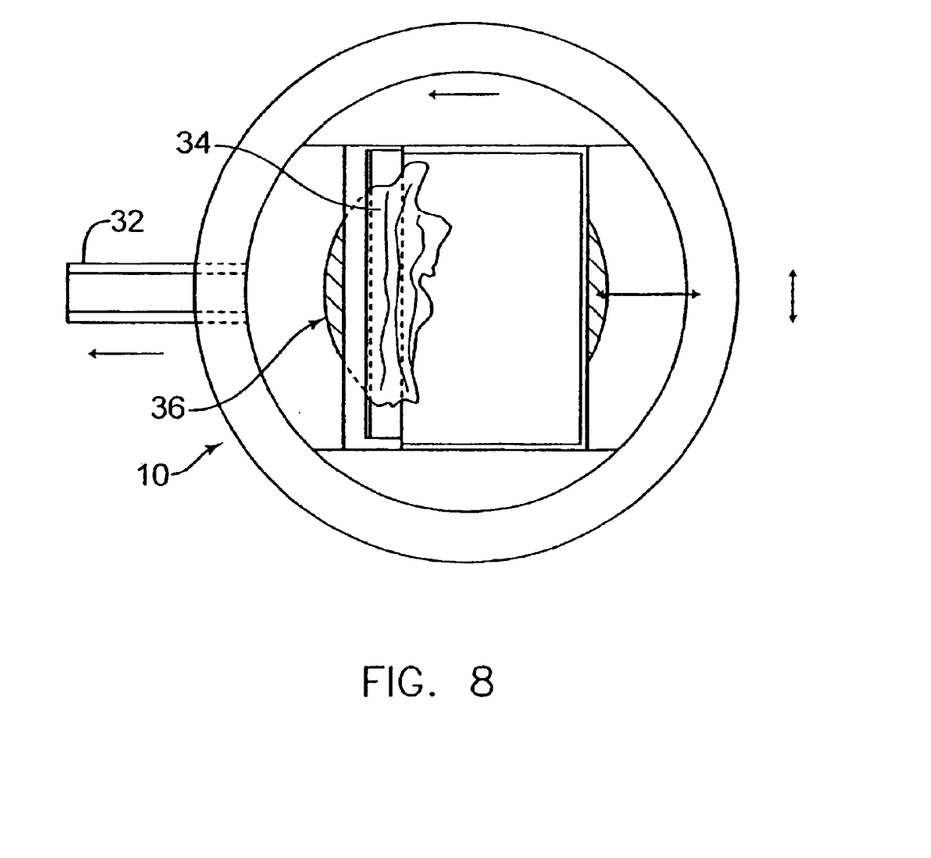
FIG. 8 is a diagram showing a top view of the eye and the separator located in a fourth position according to the preferred embodiments.

FIGS. 7 and 8 are diagrams showing a side and a top view of the eye 10 and the separator 14 located in a fourth position. In one embodiment, the travel of the separator 14 is controlled to produce an epithelial disk 34 hinged at an edge 36 of the epithelial disk 34. In another embodiment the epithelial disk 34 is completely detached for the corneal surface 18, for example, as described below.

Figure 9:
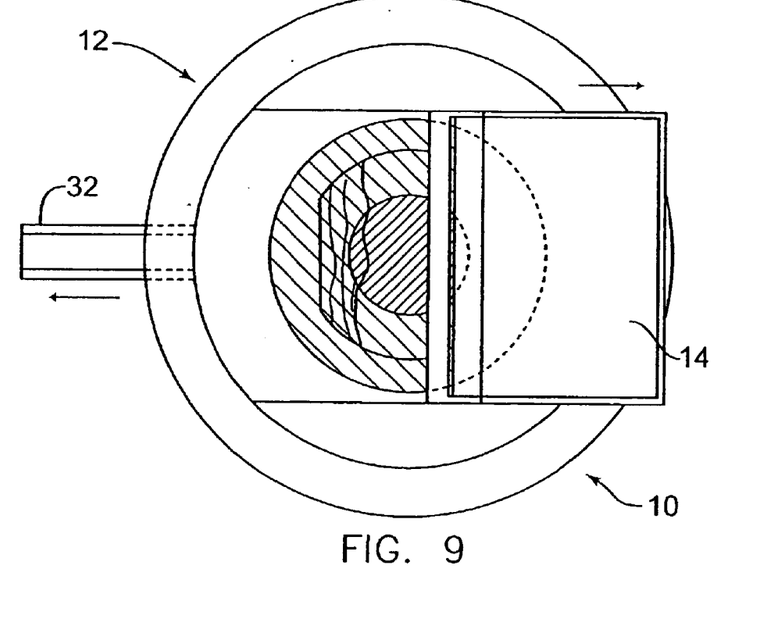
FIG. 9 is a diagram showing a top view of the eye and the separator located in a fifth position according to the preferred embodiments, the separator is retracted after epithelial separation.
Figure 10:
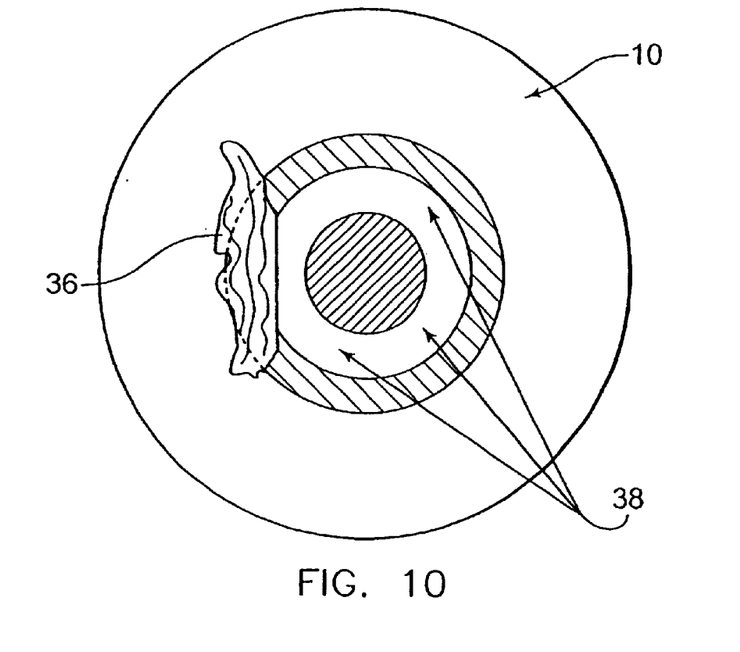
FIG. 10 is a diagram showing a top view of the eye with the separator removed.

FIG. 9 is a diagram showing a top view of the eye 10 and the separator 14 located in a retracted position after the epithelial disk 34 as been formed. After the separator 14 is retracted, suction to the circumferential groove 32 is turned off and the cornea separator device 12 is removed from the eye 10. Referring also to FIG. 10, after the cornea separator device 12 is removed, a deepithelialized area 38 is exposed that corresponds to a shape and size of the area that the separator 14 contacted during travel.

Figure 11:
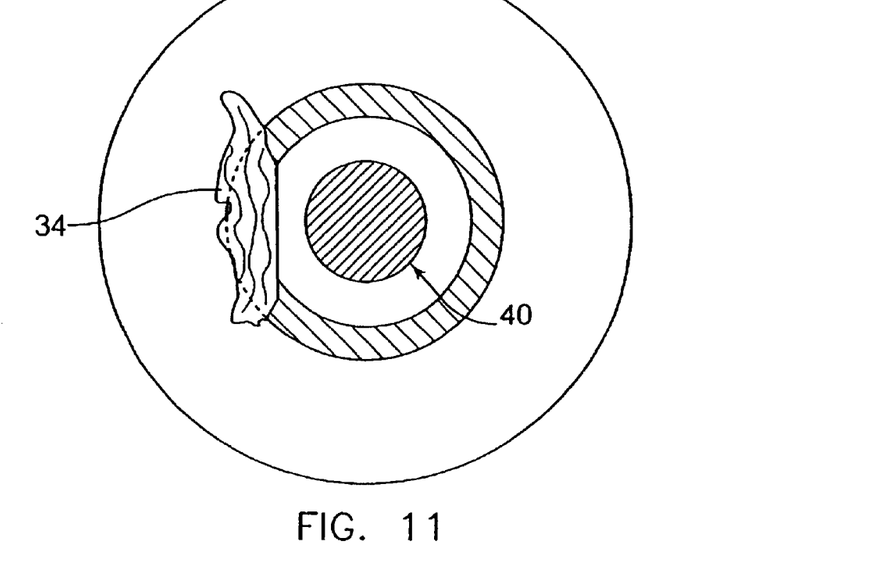
FIG. 11 is a diagram showing a top view of the eye after ablations is performed with a laser.
Figure 12:
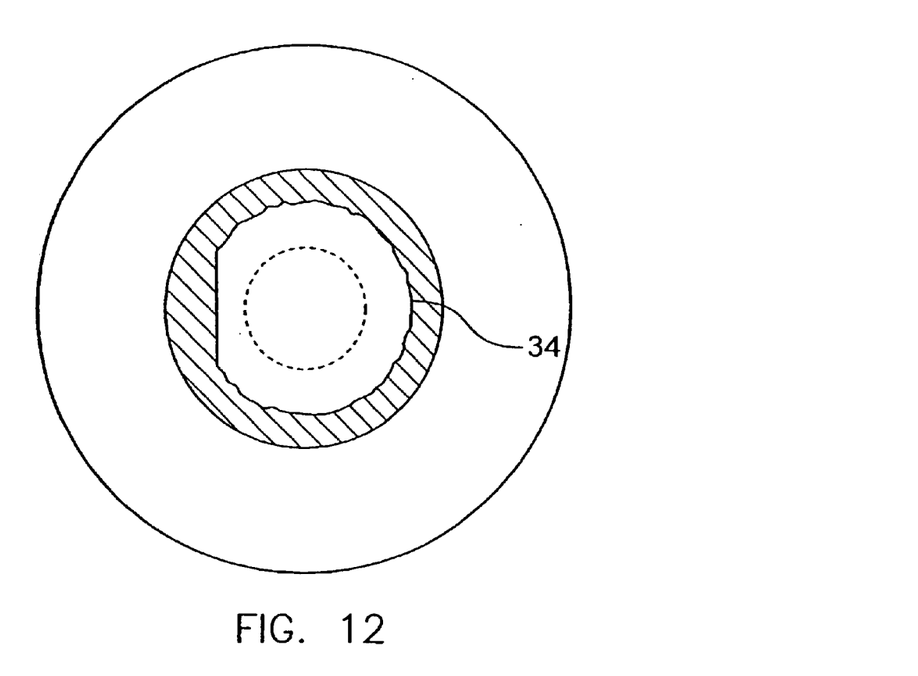
FIG. 12 is a diagram showing a top view of the eye with the epithelium replaced on the eye.
Figure 13:
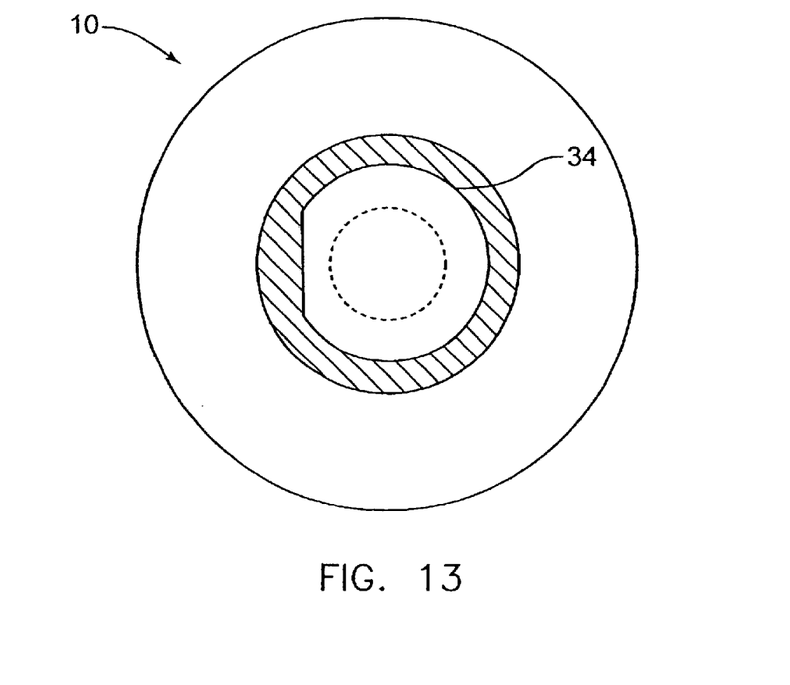
FIG. 13, is a diagram showing a top view of the eye with the epithelium smoothly stretched into place.

FIG. 11 shows a top view of the eye 10 after laser ablation is performed. The laser ablation forms an irradiated area 40 on the eye 10. Referring to FIG. 12, thereafter, the epithelium disk 34 is replaced on the corneal surface 18 of the eye 10 to aid in the healing process. Referring to FIG. 13, once replaced on the corneal surface 18, the epithelium disk 34 is preferably smoothly stretched into place.

Figure 14:
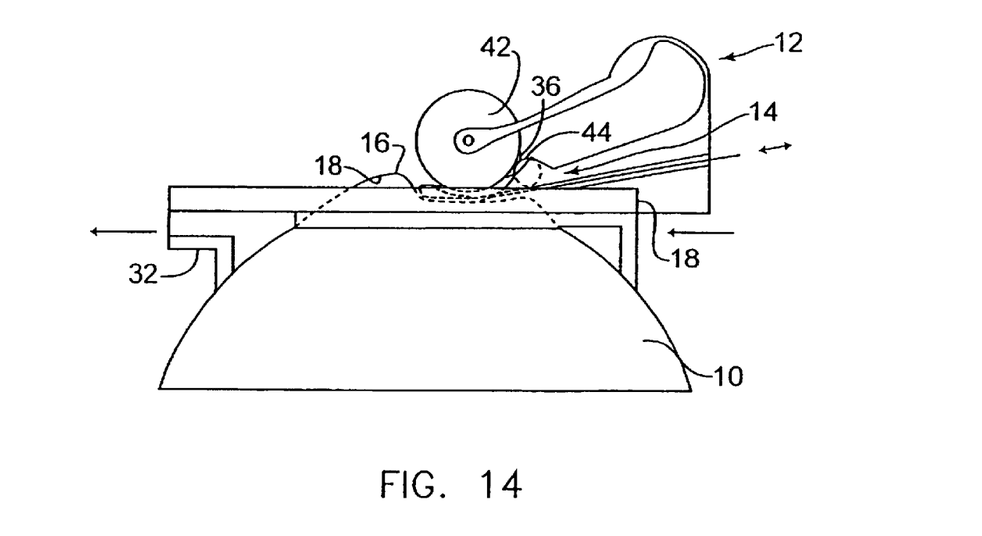
FIG. 14 is a diagram showing a side view of the eye and the cornea separator device including a rotating drum.
Figure 15:
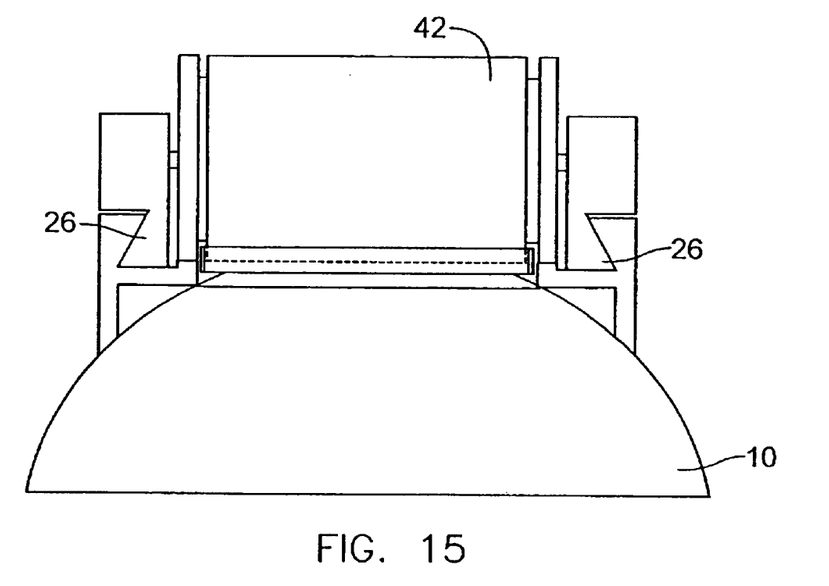
FIG. 15 is a diagram showing a front view of the eye and the cornea separator device including the rotating drum.
Figure 16:
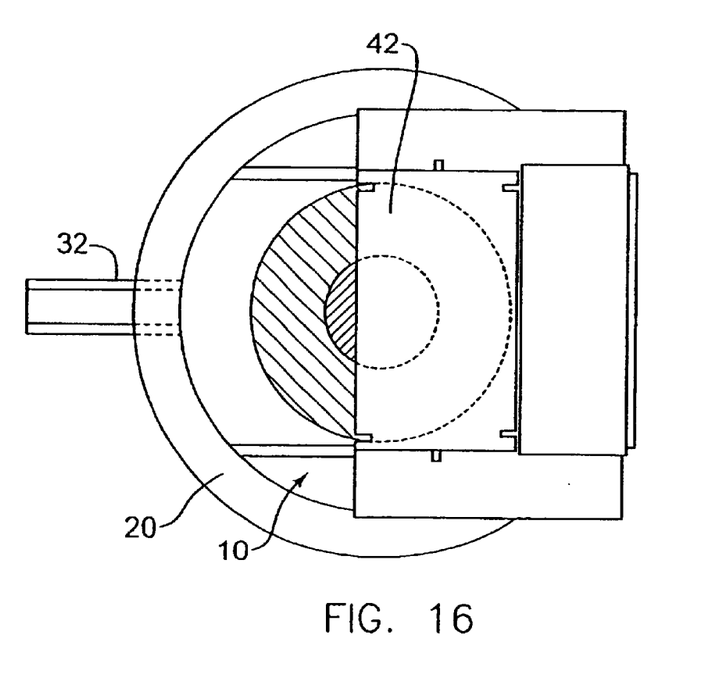
FIG. 16 is a diagram showing a top view of the eye and the cornea separator device including the rotating drum.

FIG. 14 is a diagram showing a side view of the eye 10 and the cornea separator device 12 including rotating drum 42. To rotate the drum 42, the cornea separator device 12 may include a rotating gear 44. The gear 44 could also be used to provide movement to the separator support 28. Referring also to FIGS. 15 and 16, front and top views, respectively, of the cornea separator device 12, the rotating gears 44 could be bilaterally placed on the separator support 28. The oscillating device 30 can provide for rotation of the gears 44 and the gears 44 can travel on rails, for example toothed rails, which run parallel to the groove 26.

Figure 17:
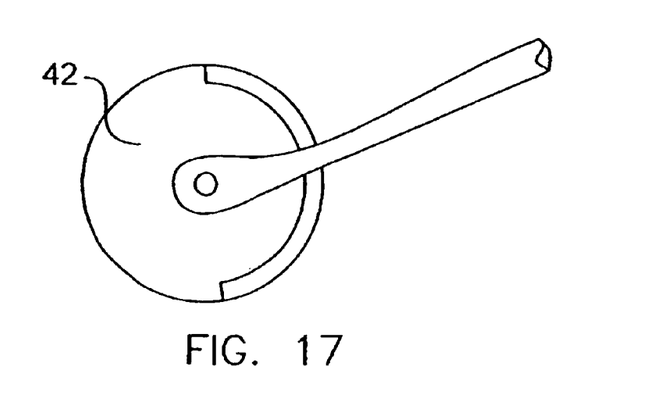
FIG. 17 is a diagram showing a drum according to one embodiment.

Since a typical thickness of an epithelial disk 36 includes about 50 microns, to preserve an epithelial disk 36, a separated epithelial disk 36 is rolled onto the drum 42. The drum 42 can include a diameter ranging from about 3 to about 9 mm and a length of about 12 mm. Referring also to FIG. 17, in one embodiment, to maintain integrity of the epithelial disk 36, the drum 42 can be coated with a hydrating and/or a conditioning substrate. The hydrating and/or conditioning substrate can include, for example, HEMA contact lenses, tissue culture media, silicone and biocompatible hydrogels. The hydrating and/or conditioning substrate can be removed from the drum after the epithelial disk 36 attaches on to the drum. Thereafter, the epithelial disk 36 can be removed from the drum 46 and replaced on the corneal surface 16, as described above.

Figure 18:
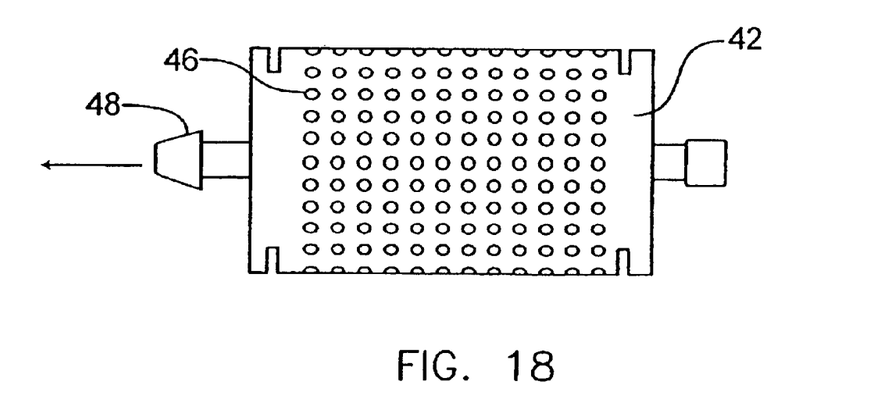
FIG. 18 is a diagram showing a drum according to another embodiment.

FIG. 18 shows another embodiment of the drum 42 includes apertures 46 and a connector 48 that connects to a suction source (not shown). By applying suction to the apertures 46 of the drum 42, the epithelial disk 36 can be rolled onto the drum 42. Thereafter, the epithelial disk 36 can be removed from the drum 46 and replaced on the corneal surface 16, as described above.

While the invention has been described above by reference to various embodiments, it will be understood that many changes and modifications can be made without departing from the scope of the invention. It is therefore intended that the foregoing detailed description be understood as an illustration of the presently preferred embodiments of the invention, and not as a definition of the invention. It is only the following claims, including all equivalents, which are intended to define the scope of this invention.

We claim:

1. A mechanical device to at least partially separate a portion of an epithelial material of a cornea from said cornea, the device comprising:
   means for separating at least partially said portion of said epithelial material from said cornea; and
   a rotating drum positioned relative to said means for separating so as to be able to receive said separated portion of said epithelial material from said separator.

2. The device as claimed in claim 1 further comprising a seating positioned on said cornea, wherein said seating has an internal diameter of at least about 10 mm.

3. The device as claimed in claim 2 where said seating includes a port through which suction is applied to ensure stable mounting of said seating to said cornea.

4. The device as claimed in claim 2, further including a separator support coupled to said means for separating, wherein said separator support is movable along a track of said seating.

5. The device as claimed in claim 4, further including a movement device coupled to said separator support, wherein said movement device is capable of moving said separator support along said track.

6. The device as claimed in claim 2, further comprising a separator support that is slidably engaged to a track of said seating to guide said means for separating on a determined path of travel.

7. The device as claimed in claim 6 where said means for separating is not sharp enough to incise corneal tissue while separating said portion of said epithelial material from said cornea.

8. The device as claimed in claim 1 further comprising a movement device that controls movement of said means for separating along said determined path of travel.

9. The device as claimed in claim 1 where said means for separating is not sharp enough to incise corneal tissue while separating said portion of said epithelial material from said cornea.

10. The device as claimed in claim 1 further comprising a movement device that controls movement of said means for separating.

11. The device as claimed in claim 1 further comprising:
    a separator support attached to said means for separating; and
    a member that engages said separator support, where a motion of said separator support is generated in response to said member moving relative to said separator support and said member travels along a track.

12. The device as claimed in claim 11, wherein said rotating drum is rotatable via friction between said member and said track as said means for separating moves along a second track of said separator support.

13. The device as claimed in claim 11, wherein said member is a rotating member.

14. The device as claimed in claim 11, wherein said means for separating is capable of oscillating during said movement across said seating.

15. The device as claimed in claim 11, wherein said member is a gear and said track is a toothed rail that is engaged by said gear when said gear rotates.

16. The device as claimed in claim 1 wherein said drum includes a diameter ranging from about 3 to about 9 mm.

17. The device as claimed in claim 1 where said drum is coated with at least one of a hydrating substrate and a conditioning substrate.

18. The device as claimed in claim 17 where said at least one of said hydrating substrate and conditioning substrate is selected from the group consisting of a HEMA contact lens, a tissue culture media, a silicone and a biocompatible hydrogel.

19. The device as claimed in claim 17 where said at least one of said hydrating substrate and said conditioning substrate can be removed from said drum after said portion of said epithelial material is received by said drum.

20. The device as claimed in claim 1 where said drum includes a hollow portion.

21. The device as claimed in claim 20 where a surface of said drum includes a hole.

22. The device as claimed in claim 21 where said hole communicates with said hollow portion of said drum which is in fluid connection with an air suction source.

23. The device as claimed in claim 1, further comprising an oscillation device coupled to said means for separating that is capable of providing motion and vibration to said means for separating.

24. The device as claimed in claim 1, further comprising a seating on said cornea, where said seating includes a port through which suction is applied to said cornea to ensure stable mounting of said seating on said cornea.

25. The device as claimed in claim 1, wherein said means for separating comprises a dull edge that separates said epithelial layer from said cornea.

26. The device as claimed in claim 25, wherein said means for separating is movable across said cornea during separation of said portion of said epithelial material and said dull edge is unable to cut said cornea as said means for separating moves across said cornea during said separation of said portion of said epithellal material.

27. The device as claimed in claim 1, wherein said drum lacks graduations.

28. The device as claimed in claim 1, wherein there is only one means for separating.

29. The device as claimed in claim 1, wherein said means for separating comprises an edge that is translatable along a plane and said drum is rotatable about an axis that is parallel to said plane.

30. The device as claimed in claim 1, wherein said drum and said means for separating are connected to one another, and said means for separating is capable of traveling across said cornea as said portion of said epithelial material is separated by said means for separating.

31. The device as claimed in claim 1, further comprising a seating which rests on said cornea, wherein said seating, said means for separating and said drum are connected to one another.

32. The device as claimed in claim 31, further comprising a moving device that is capable of moving said means for separating across said seating as said separator separates said portion of said epithelial material from said cornea.

33. The device as claimed in claim 1, further comprising:
    an engagement surface spaced from said drum; and
    a moving device that is capable of moving said means for separating and said engagement surface across said cornea, wherein during such movement said engagement surface flattens said portion of said epithelial material.

34. The device as claimed in claim 33, wherein said means for separating is unable to substantially incise said cornea as said means for separating separates said portion of said epithelial material.

35. The device as claimed in claim 1, wherein said separated portion of said epitheliai material remains a part of said epithelial material during said separating.

36. The device as claimed in claim 1, further comprising:
an engagement surface spaced from said means for separating; and
a moving device that is capable of moving said means for separating across said cornea, wherein during such movement said engagement surface flattens said portion of said epithelial material.

37. The device of claim 1, wherein said means for separating comprises a dull edge that has a dimension that is greater than the size of a radius of a pupil of an eye that includes said epithelial material.

38. The device of claim 1, wherein said means for separating has a structure so as to separate said portion of said epithelial material from said cornea without the assistance of any chemicals.

39. The device of claim 1, further including a movement device, wherein said movement device is capable of generating through said means for separating a mechanical force that is sufficient to separate said portion of said epithelial material from said cornea, but insufficient to cut said corneal stroma over a distance that is greater than a radius of a pupil.

40. The device of claim 1, further including a movement device, wherein said movement device is capable of causing said means for separating to move a distance across said cornea that corresponds to at least a radius of a pupil of an eye that includes said epithelial material.

41. The device of claim 40, wherein said means for separating separates said portion of said epithelial material and does not cut said corneal stroma while moving along said distance.

42. The device of claim 40 wherein said movement device is capable of moving said means for separating so that said means for separating is capable of moving along a majority of a length of a track wherein said means for separating does not cut said corneal stroma anywhere along said majority of said length of said track, wherein said track corresponds to at least a radius of a pupil of an eye that includes said epithelial material.

43. The device of claim 42, wherein a length of said track is at least 6 mm.

44. A mechanical device to at least partially separate a portion of an epithelial material of a cornea from said cornea, the device comprising:
a means for separating at least partially said portion of said epithelium material from said cornea, wherein said means for separating is capable of oscillating with a frequency ranging from about 10 Hz to about 10 KHz; and
a rotating drum positioned relative to said means for separating so as to be able to receive said separated portion of said epithelial material from said means for separating and to be able to roll said separated portion of said epithelium material at least partially upon said drum.

45. The device as claimed in claim 44 where said means for separating is capable of oscillating via electromagnetic forces acting on said means for separating.

46. The device as claimed in claim 44 where said means for separating is capable of oscillating via piezoelectric forces acting on said means for separating.

47. The device as claimed in claim 44, wherein said separated portion of said epithelial material remains a part of said epithelial material during said separating.

48. A device that separates at least partially and receives at least partially a portion of an epithelial material of a cornea from said cornea, the device comprising:
means for separating at least partially said portion of said epithelial material from said cornea; and
a movable surface that is movable relative to said means for separating and is positioned so as to be able to receive said separated portion of said epithelial material.

49. The device according to claim 48 wherein said movable surface substantially securely holds said separated portion of said epithelial material.

50. The device according to claim 48, wherein said surface has a structure that substantially preserves said separated portion of said epithelial material.

51. The device according to claim 50, wherein said surface comprises a coating.

52. The device according to claim 51, wherein said coating is a hydrating substance that hydrates said separated portion of said epithelial material.

53. The device according to claim 51, wherein said coating is a conditionIng substance that conditions said separated portion of said epithelial material.

54. The device according to claim 51, where said coating is selected from the group consisting of: a HEMA a contact lens, a tissue culture media, a silicone and a biocompatible hydrogel.

55. The device according to claim 51, wherein said coating is removable.

56. The device according to claim 49, further comprising a suction source in fluid communication with said movable surface for assisting said movable surface in holding said separated portion of said epithelial material.

57. The device according to claim 56, wherein said movable surface defines at least one aperture through which said suction source applies suction.

58. The device according to claim 49, wherein said separator separates a lower surface of said portion of said epithelial material from said cornea and said movable surface is positioned so that said lower surface lies upon said movable surface.

59. The device according to claim 48, wherein said movable surface has a structure that substantially preserves said separated portion of said epithelial material.

60. The device according to claim 48, wherein said movable surface is capable of moving in a rotational direction about an axis of rotation.

61. The device according to claim 48, wherein said means for separating is capable of separating a lower surface of said portion of said epithelial material from said cornea and said movable surface is positioned so that said lower surface is capable of lying upon said movable surface.

62. The device according to claim 48, wherein said means for separating is not able to substantially cut corneal tissue during separation of said portion of said epithelial material by said means for separating.

63. The device according to claim 48, further comprising a seating that engages said means for separating and defines a path of travel of said means for separating.

64. The device as claimed in claim 48, wherein said separated portion of said epithelial material remains a part of said epithelial material.

65. The device as claimed in claim 48, wherein said movable surface is movable independently of said separator.

66. The device as claimed in claim 48, further comprising:
an engagement surface spaced from said means for separating; and
a moving device that is capable of moving said means for separating across said cornea, wherein during such movement said engagement surface flattens said portion of said epithelial material.

67. The device of claim 48, wherein said means for separating comprises a dull edge that has a dimension that is greater than the size of a radius of a pupil of an eye that includes said epithelial material.

68. The device of claim 48, wherein said means for separating has a structure so as to separate said portion of said epithelial material from said cornea without the assistance of any chemicals.

69. The device as claimed in claim 48 further comprising:
a seating positioned on said cornea;
a separator support coupled to said means for separating, wherein said separator support is movable along a track of said seating; and
a movement device coupled to said separator support, wherein said movement device is capable of moving said separator support along said track.

70. The device of claim 69, wherein said movement device is capable of generating through said means for separating a mechanical force that is sufficient to separate said portion of said epithelial material from said cornea, but insufficient to cut said corneal stroma.

71. The device of claim 69, wherein said movement device causes said means for separating to move a distance across said cornea that corresponds to at least a radius of a pupil of an eye that includes said epithelial material.

72. The device of claim 71, wherein said movement device is capable of moving said means for separating along a distance of at least 6 mm, wherein said means for separating is capable of separating said portion of said epithelial material and does not cut said corneal stroma while moving along said distance.

73. The device of claim 69 wherein said movement device is capable of moving said means for separating so that said means for separating is capable of moving along a majority of a length of said track wherein said means for separating does not cut said corneal stroma anywhere along said majority of said length of said track.

74. The device of claim 69, wherein a length of said track is at least 6 mm.

75. A mechanical device to at least partially separate a portion of an epithelial material of a cornea from said cornea, the device comprising:
a separator having a structure to at least partially separate said portion of said epithelium material from said cornea, wherein said separator is capable of oscillating with a frequency ranging from about 10 Hz to about 10 KHz; and
a rotating drum positioned relative to said separator so as to be able to receive said separated portion of said epithelial material from said separator and to be able to roll said separated portion of said epithelium material at least partially upon said drum.

76. The device of claim 75, further including a movement device, wherein said movement device is capable of causing said separator to move a distance across said cornea that corresponds to at least a radius of a pupil of an eye that includes said epithelial material.

77. The device of claim 75, wherein said separator comprises an edge that contacts said epithelial material so as to at least partially separate said portion of said epithelial material from said cornea.

* * * * *

UNITED STATES PATENT AND TRADEMARK OFFICE
CERTIFICATE OF CORRECTION

| | | |
|---|---|---|
| PATENT NO. | : 7,156,859 B2 | Page 1 of 1 |
| APPLICATION NO. | : 09/911356 | |
| DATED | : January 2, 2007 | |
| INVENTOR(S) | : Ioannis Pallikaris et al. | |

It is certified that error appears in the above-identified patent and that said Letters Patent is hereby corrected as shown below:

In the Claims

In column 5, claim 8, line 35, before "further comprising" replace "1" with --6--.

In column 6, claim 35, line 67, after "portion of said" replace "epitheliai" with --epithelial--.

In column 8, claim 50, line 8, after "wherein said" insert --movable--.

In column 8, claim 51, line 11, after "wherein said" insert --movable--.

In column 8, claim 53, line 17, after "coating is a" replace "conditionIng" with --conditioning--.

Signed and Sealed this

Seventh Day of September, 2010

David J. Kappos
*Director of the United States Patent and Trademark Office*